(12) United States Patent
Sameshima (10) Patent No.: US 10,126,253 B2
(45) Date of Patent: Nov. 13, 2018

(54) PHOTOINDUCED CARRIER LIFETIME MEASUREMENT DEVICE AND PHOTOINDUCED CARRIER LIFETIME MEASUREMENT METHOD

(71) Applicant: NATIONAL UNIVERSITY CORPORATION TOKYO UNIVERSITY OF AGRICULTURE AND TECHNOLOGY, Fuchu-shi, Tokyo (JP)

(72) Inventor: Toshiyuki Sameshima, Fuchu (JP)

(73) Assignee: National University Corporation Tokyo University of Agriculture and Technology (JP)

( * ) Notice: Subject to any disclaimer, the term of this patent is extended or adjusted under 35 U.S.C. 154(b) by 1177 days.

(21) Appl. No.: 14/364,997

(22) PCT Filed: Dec. 11, 2012

(86) PCT No.: PCT/JP2012/082038
§ 371 (c)(1),
(2) Date: Jun. 12, 2014

(87) PCT Pub. No.: WO2013/089088
PCT Pub. Date: Jun. 20, 2013

(65) Prior Publication Data
US 2014/0303919 A1    Oct. 9, 2014

(30) Foreign Application Priority Data

Dec. 16, 2011    (JP) .................................. 2011-276215
Nov. 19, 2012    (JP) .................................. 2012-253129

(51) Int. Cl.
*G01N 22/00*    (2006.01)
*H01L 21/66*    (2006.01)
(Continued)

(52) U.S. Cl.
CPC ............. *G01N 22/00* (2013.01); *G01N 21/63* (2013.01); *G01N 27/00* (2013.01); *G01N 33/00* (2013.01);
(Continued)

(58) Field of Classification Search
CPC ........ G01N 22/00; G01N 21/63; G01N 27/00; G01N 33/00; G01N 2033/0095; G01R 31/2642; G01R 31/2656; H01L 22/12
See application file for complete search history.

(56) References Cited

U.S. PATENT DOCUMENTS 4,949,034 A * 8/1990 Imura .................. G01R 31/308
                                                                    324/642
5,153,503 A * 10/1992 Yahata ................ G01N 21/6489
                                                                    324/73.1
(Continued)

FOREIGN PATENT DOCUMENTS

JP      2005-277417 A    10/2005
JP      2011-082312 A    4/2011
WO      WO-2011-099191 A1    8/2011

OTHER PUBLICATIONS

J. M. Borrego, R. J. Gutmann, N. Jensen and O. Paz, "Non-Destructive Lifetime Measurement in Silicon Wafers by Microwave Reflection", Solid-State Electronics, vol. 30, No. 2, pp. 195-203, 1987.
(Continued)

*Primary Examiner* — John Breene
*Assistant Examiner* — Yaritza H Perez Bermudez
(74) *Attorney, Agent, or Firm* — Harness, Dickey & Pierce, P.L.C.

(57) ABSTRACT

A photoinduced carrier lifetime measurement device includes light sources that respectively apply light that differs in wavelength and generates photoinduced carriers to a semiconductor substrate, a microwave generation section
(Continued)

that generates microwaves that are applied to the semiconductor substrate, a detection section that detects the intensity of the microwaves that have passed through the semiconductor substrate, and a calculation section that calculates the effective carrier lifetime corresponding to the wavelength of each light based on the intensity of the microwaves detected when applying each light, and calculates the bulk carrier lifetime and a surface recombination velocity of the semiconductor substrate based on the effective carrier lifetime calculated corresponding to the wavelength of each light.

12 Claims, 5 Drawing Sheets

(51) Int. Cl.
| | | |
|---|---|---|
| *G01N 21/63* | (2006.01) | |
| *G01N 27/00* | (2006.01) | |
| *G01N 33/00* | (2006.01) | |
| *G01R 31/26* | (2014.01) | |
| *G01R 31/265* | (2006.01) | |

(52) U.S. Cl.
CPC .......... *G01R 31/2642* (2013.01); *H01L 22/12* (2013.01); *G01N 2033/0095* (2013.01); *G01R 31/2656* (2013.01)

(56) References Cited

U.S. PATENT DOCUMENTS

| | | | | |
|---|---|---|---|---|
| 2005/0206402 A1* | 9/2005 | Shi | ................. | G01R 31/311 324/754.23 |
| 2006/0094133 A1* | 5/2006 | Takeuchi | ........... | G01N 21/1717 438/14 |
| 2007/0126458 A1 | 6/2007 | Shi et al. | | |
| 2012/0203473 A1* | 8/2012 | Hayashi | ................. | G01N 21/31 702/34 |
| 2012/0310556 A1* | 12/2012 | Sameshima | ............ | G01N 22/00 702/58 |
| 2013/0169283 A1* | 7/2013 | Lagowski | ............ | G01R 31/305 324/501 |
| 2013/0278749 A1* | 10/2013 | Mandelis | ................. | H04N 5/33 348/87 |

OTHER PUBLICATIONS

G. S. Kousik, Z. G. Ling, and P. K. Ajmera, "Nondestructive technique to measure bulk lifetime and surface recombination velocities at the two surfaces by infrared absorption due to pulsed optical excitation", J. Appl. Phys. vol. 72 (1), pp. 141-146, Jul. 1, 1992.

Toshiyuki Sameshima, Hiromi Hayasaka, and Tomonori Haba, "Analysis of Microwave Absorption Caused by Free Carriers in Silicon", Japanese Journal of Applied Physics, vol. 48, pp. 021204-1-021204-6, (2009).

Toshiyuki Sameshima, Tomokazu Nagao, Shinya Yoshidomi, Kazuya Kogure, and Masahiko Hasumi, "Minority Carrier Lifetime Measurements by Photoinduced Carrier Microwave Absorption Method", Japanese Journal of Applied Physics, vol. 50, pp. 03CA02-1-03CA02-08, (2011).

Office Action for Chinese Patent Application Serial No. 2016022901369840 dated Mar. 3, 2016 with translation (12 pages).

* cited by examiner

PHOTOINDUCED CARRIER LIFETIME MEASUREMENT DEVICE AND PHOTOINDUCED CARRIER LIFETIME MEASUREMENT METHOD

CROSS-REFERENCE TO RELATED APPLICATIONS

This application is a U.S. National Stage Application of International Application No. PCT/JP2012/082038 filed on Dec. 11, 2012, and published in Japanese as WO 2013/089088 A1 on Jun. 20, 2013. This application claims priority to Japanese Application Nos. 2011-276215 filed on Dec. 16, 2011 and 2012-253129 filed on Nov. 19, 2012. The disclosures of the above applications are incorporated herein by reference.

TECHNICAL FIELD

The present invention relates to a photoinduced carrier lifetime measurement device and a photoinduced carrier lifetime measurement method.

BACKGROUND ART

A μ-PCD method has been known as a method for measuring the effective carrier lifetime of photoinduced carriers (minority carriers) generated in a semiconductor substrate (see J. M. Borrego, R. J. Gutmann, N. Jensen, and O. Paz: *Solid-Sate Electron.*, 30, 195 (1987), for example). The μ-PCD method applies an ultrashort light pulse to the semiconductor substrate in a state in which microwaves are applied to the semiconductor substrate. The microwaves are reflected by carriers induced by the light pulse, and a temporal change in reflection intensity is measured to determine the effective carrier lifetime of the photoinduced carriers.

A QSSPC method has also been known as a method for measuring the effective carrier lifetime of photoinduced carriers generated in a semiconductor substrate (see G. S. Kousik, Z. G. Ling, and P. K. Ajmera: *J. Appl. Phys.*, 72, 141 (1992), for example). According to the QSSPC method, an inductance coil is disposed to face the semiconductor substrate, and radio frequency (RF) electromagnetic waves are applied to the semiconductor substrate. An ultrashort light pulse is also applied to the semiconductor substrate. The RF electromagnetic waves are reflected by carriers induced by the light pulse, and a temporal change in reflected waves is measured as a change in current that flows through the coil to determine the effective carrier lifetime of the photoinduced carriers.

A microwave optical interference absorption method has also been known as a method for measuring the effective carrier lifetime of photoinduced carriers generated in a semiconductor substrate (see T. SAMESHIMA, H. HAYASAKA, and T. HABA: *Jpn. J. Appl. Phys.* 48 (2009) 021204-1-6, for example). According to the microwave optical interference absorption method, the semiconductor substrate is inserted into a microwave interferometer that is formed using a waveguide, and continuous light is applied to the semiconductor substrate in a state in which microwaves are applied to the semiconductor substrate. The microwaves are absorbed by carriers induced by the continuous light, and a decrease in microwave transmittance is measured to determine the effective carrier lifetime of the photoinduced carriers.

A method has been known that applies periodic intermittent pulsed light to the semiconductor substrate when implementing the method described in (see Toshiyuki Sameshima, Tomokazu Nagao, Shinya Yoshidomi, Kazuya Kogure, and Masahiko Hasumi: "Minority Carrier Lifetime Measurements by Photo-Induced Carrier Microwave Absorption Method", *Jpn. J. Appl. Phys.* 50 (2011) 03CA02, and WO11/099,191, for example). According to this method, the effective carrier lifetime can be calculated regardless of the intensity of irradiation light by changing the irradiation time and the cycle of the pulsed light.

SUMMARY OF THE INVENTION

Technical Problem

The effective carrier lifetime of photoinduced carriers generated in a semiconductor substrate can be measured using the above techniques. The effective carrier lifetime of photoinduced carriers is normally determined by the lifetime (bulk carrier lifetime) specific to the semiconductor substrate, and the surface recombination velocity that depends on surface defects of the semiconductor substrate. When producing a device (e.g., solar cell or CCD) that effectively utilizes photoinduced carriers, it is important to increase the effective carrier lifetime by increasing the bulk carrier lifetime, and decreasing the surface recombination velocity. It is desirable that the bulk carrier lifetime and the surface recombination velocity can be experimentally obtained using an effective carrier lifetime measurement device (analyzer).

However, known techniques can precisely calculate the effective carrier lifetime, but cannot determine both the bulk carrier lifetime and the surface recombination velocity. Specifically, known techniques generally presume one of the bulk carrier lifetime and the surface recombination velocity, and determine the other of the bulk carrier lifetime and the surface recombination velocity. For example, since it is considered that an indirect energy band-type crystalline semiconductor (e.g., silicon) has a long bulk carrier lifetime, the bulk carrier lifetime is normally presumed to be sufficiently long, and the surface recombination velocity is determined from the measured effective carrier lifetime. However, since the presumed bulk carrier lifetime involves uncertainty, a problem may occur when it is desired to implement precise analysis.

The invention was conceived in view of the above problem. An object of the invention is to provide a photoinduced carrier lifetime measurement device and a photoinduced carrier lifetime measurement method that can accurately measure the bulk carrier lifetime and the surface recombination velocity of a semiconductor substrate.

Solution to Problem (1) According to one aspect of the invention, there is provided a photoinduced carrier lifetime measurement device that measures the effective carrier lifetime of photoinduced carriers generated in a semiconductor substrate, the photoinduced carrier lifetime measurement device including:

an irradiation section that applies at least two types of light to the semiconductor substrate, the at least two types of light differing in wavelength, and generating the photoinduced carriers;

a microwave generation section that generates microwaves that are applied to the semiconductor substrate;

a detection section that detects the intensity of the microwaves that have passed through the semiconductor substrate; and a calculation section that calculates the effective carrier lifetime based on the intensity of the microwaves detected by the detection section, the calculation section calculating the effective carrier lifetime corresponding to the wavelength of each of the at least two types of light based on the intensity of the microwaves detected when applying each of the at least two types of light, and calculating the bulk carrier lifetime and the surface recombination velocity of the semiconductor substrate based on the effective carrier lifetime calculated corresponding to the wavelength of each of the at least two types of light.

According to another aspect of the invention, there is provided a photoinduced carrier lifetime measurement method that measures the effective carrier lifetime of photoinduced carriers generated in a semiconductor substrate, the photoinduced carrier lifetime measurement method including:

applying at least two types of light to the semiconductor substrate, and applying microwaves to the semiconductor substrate, the at least two types of light differing in wavelength, and generating the photoinduced carriers;

detecting the intensity of the microwaves that have passed through the semiconductor substrate; and calculating the effective carrier lifetime corresponding to the wavelength of each of the at least two types of light based on the intensity of the microwaves detected when applying each of the at least two types of light, and calculating the bulk carrier lifetime and the surface recombination velocity of the semiconductor substrate based on the effective carrier lifetime calculated corresponding to the wavelength of each of the at least two types of light.

According to the aspects of the invention, the bulk carrier lifetime and the surface recombination velocity can be accurately measured by calculating the effective carrier lifetime corresponding to the wavelength of each of the at least two types of light based on the intensity of the microwaves detected when applying each of the at least two types of light, and calculating the bulk carrier lifetime and the surface recombination velocity of the semiconductor substrate based on the effective carrier lifetime calculated corresponding to the wavelength of each of the at least two types of light.

(2) In the photoinduced carrier lifetime measurement device and the photoinduced carrier lifetime measurement method, a calculated value of the effective carrier lifetime calculated corresponding to the wavelength of each of the at least two types of light using the bulk carrier lifetime and the surface recombination velocity as parameters may be compared with a measured value of the effective carrier lifetime calculated corresponding to the wavelength of each of the at least two types of light based on the detected intensity of the microwaves while changing values of the parameters to determine the bulk carrier lifetime and the surface recombination velocity when the calculated value of the effective carrier lifetime calculated corresponding to the wavelength of each of the at least two types of light is in best conformity with the measured value of the effective carrier lifetime calculated corresponding to the wavelength of each of the at least two types of light.

This makes it possible to measure both the bulk carrier lifetime and the surface recombination velocity of the semiconductor substrate without presuming the bulk carrier lifetime or the surface recombination velocity.

(3) In the photoinduced carrier lifetime measurement device and the photoinduced carrier lifetime measurement method, a calculated value of the effective carrier lifetime calculated corresponding to the wavelength of each of the at least two types of light using a depthwise distribution of the bulk carrier lifetime and the surface recombination velocity as parameters may be compared with a measured value of the effective carrier lifetime calculated corresponding to the wavelength of each of the at least two types of light based on the detected intensity of the microwaves while changing values of the parameters to determine the depthwise distribution of the bulk carrier lifetime and the surface recombination velocity when the calculated value of the effective carrier lifetime calculated corresponding to the wavelength of each of the at least two types of light is in best conformity with the measured value of the effective carrier lifetime calculated corresponding to the wavelength of each of the at least two types of light.

This makes it possible to measure both the depthwise distribution of the bulk carrier lifetime and the surface recombination velocity of the semiconductor substrate without presuming the depthwise distribution of the bulk carrier lifetime or the surface recombination velocity.

(4) In the photoinduced carrier lifetime measurement device and the photoinduced carrier lifetime measurement method, a carrier generation rate may be calculated based on an effective carrier lifetime of a reference sample, prepared by forming a passivation film on a surface of the semiconductor substrate, that is calculated based on the intensity of the microwaves detected when applying periodic pulsed light to the reference sample, and a sheet carrier density of the reference sample calculated based on the intensity of the microwaves detected when applying continuous light to the reference sample, and the measured value of the effective carrier lifetime may be calculated based on the sheet carrier density of the semiconductor substrate as a measurement target sample calculated based on the intensity of the microwaves detected when applying continuous light to the semiconductor substrate, and the carrier generation rate.

This makes it possible to accurately calculate the measured value of the effective carrier lifetime.

(5) In the photoinduced carrier lifetime measurement device and the photoinduced carrier lifetime measurement method, the at least two types of light may differ in absorption coefficient with respect to the semiconductor substrate.

(6) In the photoinduced carrier lifetime measurement device and the photoinduced carrier lifetime measurement method, the at least two types of light may differ in absorption coefficient with respect to the semiconductor substrate by a factor of at least 2.

DESCRIPTION OF EMBODIMENTS

Exemplary embodiments of the invention are described below. Note that the following exemplary embodiments do not unduly limit the scope of the invention as stated in the claims. Note also that all of the elements described below in connection with the exemplary embodiments should not necessarily be taken as essential elements of the invention.

1. Measurement Principle

A measurement method and a measurement device according to one embodiment of the invention apply at least two types of light that differ in absorption coefficient to a semiconductor substrate (measurement target sample).

For example, when light having a short wavelength (i.e., the absorption coefficient is large) is applied to the semiconductor substrate, the light is absorbed by the top surface region of the semiconductor substrate. When the surface recombination velocity of the semiconductor substrate is high, photoinduced carriers generated in the surface region of the semiconductor substrate promptly recombine and disappear. Therefore, the carrier concentration in the semiconductor substrate decreases. Accordingly, the microwave absorption decreases (i.e., the microwave transmittance increases) when microwaves are applied to the semiconductor substrate, and the effective carrier lifetime decreases.

When light having a long wavelength (i.e., the absorption coefficient is small) is applied to the semiconductor substrate, the light reaches a deep region of the semiconductor substrate. Therefore, the effects of the surface recombination velocity decrease, and the carrier concentration increases as compared with the case of applying light having a short wavelength when the bulk carrier lifetime of the semiconductor substrate is sufficiently long. Accordingly, the effective carrier lifetime increases.

Specifically, when the effective carrier lifetime is limited by the surface recombination velocity (i.e., when the surface recombination velocity is high), the effective carrier lifetime to be measured has wavelength dependence, and the effective carrier lifetime measured from the microwave transmittance detected when applying light having a short wavelength differs from the effective carrier lifetime measured from the microwave transmittance detected when applying light having a long wavelength.

When the surface of the semiconductor substrate is passivated, and the effective carrier lifetime is limited by the bulk carrier lifetime (i.e., when the surface recombination velocity is sufficiently low), photoinduced carriers disappear over the entire semiconductor substrate in an identical ratio, and the effective carrier lifetime to be measured does not have wavelength dependence.

The surface recombination velocity and the bulk carrier lifetime of the semiconductor substrate can be evaluated by measuring the effective carrier lifetime when applying each of at least two types of light that differ in wavelength to the semiconductor substrate, and analyzing the measured effective carrier lifetimes (at least two effective carrier lifetimes).

2. Configuration

Figure 1:
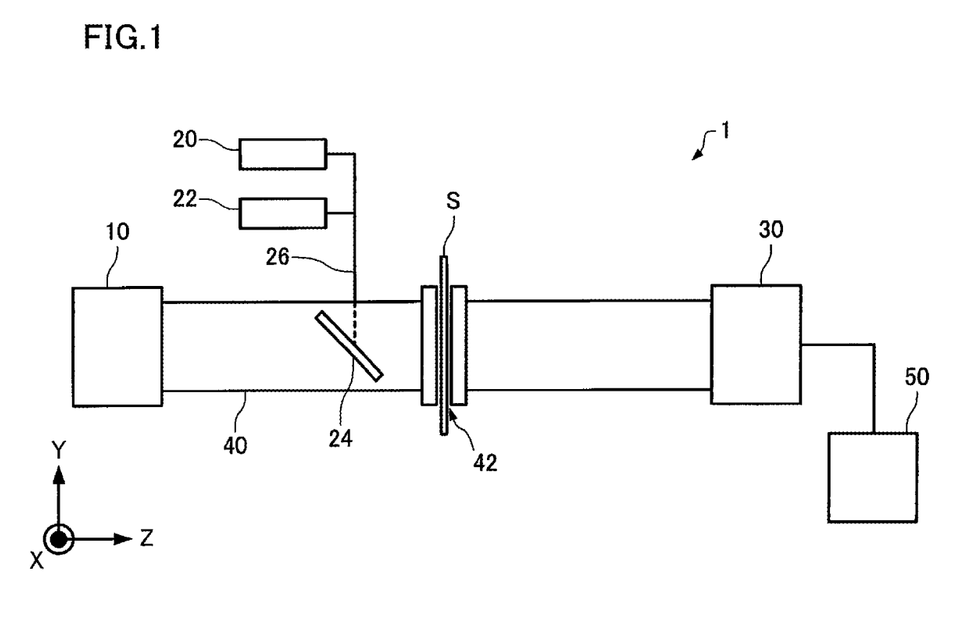
FIG. 1 is a diagram illustrating an example of the configuration of a measurement device (photoinduced carrier lifetime measurement device) according to one embodiment of the invention.

FIG. 1 is a diagram illustrating an example of the configuration of a measurement device (photoinduced carrier lifetime measurement device) according to one embodiment of the invention. A measurement device 1 according to one embodiment of the invention is configured to measure the effective carrier lifetime of a semiconductor substrate S (i.e., measurement target sample), and analyze the measured effective carrier lifetime to measure the bulk carrier lifetime and the surface recombination velocity of the semiconductor substrate S.

The measurement device 1 includes a microwave generation section 10 that generates microwaves that are applied to the semiconductor substrate S, light sources 20 and 22 (irradiation section) that apply light (induction light) for generating photoinduced carriers to the semiconductor substrate S, a detection section 30 that detects the intensity of the microwaves that have passed through the semiconductor substrate S, a waveguide 40 that propagates the microwaves generated by the microwave generation section 10 to the detection section 30, and a calculation section 50.

The waveguide 40 is provided with a gap 42 into which the semiconductor substrate S is inserted. A reflector 24 that causes light emitted from the light sources 20 and 22 to be incident on the semiconductor substrate S is provided in the waveguide 40 on the side of the microwave generation section 10 relative to the gap 42. Light emitted from the light sources 20 and 22 passes through the optical fiber 26, is diffusely reflected by the reflector 24, and is incident on the semiconductor substrate S. The reflector 24 is a Teflon (registered trademark) sheet, for example. Note that a light guide plate may be provided instead of the reflector 24 so that light emitted from the light sources 20 and 22 is incident on the semiconductor substrate S.

The light sources 20 and 22 are laser light sources, for example. Light emitted from the light source 20 and light emitted from the light source 22 differ in wavelength (i.e., differ in absorption coefficient with respect to the semiconductor substrate S). The light source 20 is a light source for applying light having a short wavelength (e.g., light that generates carriers in the surface region of the semiconductor substrate S) to the semiconductor substrate S, and the light source 22 is a light source for applying light having a long wavelength (e.g., light that generates carriers in the inner region of the semiconductor substrate S) to the semiconductor substrate S.

The calculation section 50 (computer) performs a calculation process that calculates the effective carrier lifetime of photoinduced carriers generated in the semiconductor substrate S based on microwave intensity information detected by the detection section 30, and calculates the bulk carrier lifetime and the surface recombination velocity of the semiconductor substrate S based on the calculated effective carrier lifetime.

The calculation section 50 calculates a change in microwave transmittance from the microwave intensity information detected when light having a short wavelength emitted from the light source 20 is applied to the semiconductor substrate S, and calculates the effective carrier lifetime when light emitted from the light source 20 is applied to the semiconductor substrate S (i.e., the effective carrier lifetime corresponding to the wavelength of light emitted from the light source 20) based on the calculated change in microwave transmittance. The calculation section 50 calculates a change in microwave transmittance from the microwave intensity information detected when light having a long wavelength emitted from the light source 22 is applied to the semiconductor substrate S, and calculates the effective carrier lifetime when light emitted from the light source 22 is applied to the semiconductor substrate S (i.e., the effective carrier lifetime corresponding to the wavelength of light emitted from the light source 22) based on the calculated change in microwave transmittance.

The calculation section 50 analyzes and calculates the bulk carrier lifetime $\tau_b$ and the surface recombination velocities (i.e., the surface recombination velocity $S_{top}$ on the side (irradiation side) to which the induction light is applied, and the surface recombination velocity $S_{rear}$ on the side opposite to the irradiation side) that are in best conformity with the measured effective carrier lifetimes $\tau_{eff}$ (i.e., the effective carrier lifetime measured when light emitted from the light source 20 is applied to the semiconductor substrate S, and the effective carrier lifetime measured when light emitted from the light source 22 is applied to the semiconductor substrate S). Note that the bulk carrier lifetime $\tau_b$ and the surface recombination velocities $S_{top}$ and $S_{rear}$ are analyzed taking account of the penetration depth of photocarriers.

The method for analyzing the bulk carrier lifetime $\tau_b$ and the surface recombination velocities $S_{top}$ and $S_{rear}$ that is employed for the measurement device and the measurement method is described below.

When continuous light is applied to the surface of the semiconductor substrate, the steady-state photoinduced minority carrier volume concentration n(x) at a depth x from the surface (irradiation side) is given by the following differential expression. Note that D is the diffusion coefficient of minority carriers in the semiconductor substrate.

$$D\frac{\partial^2 n(x)}{\partial x^2} + G(x) - \frac{n(x)}{\tau_b} = 0 \quad (1)$$

Figure 2:
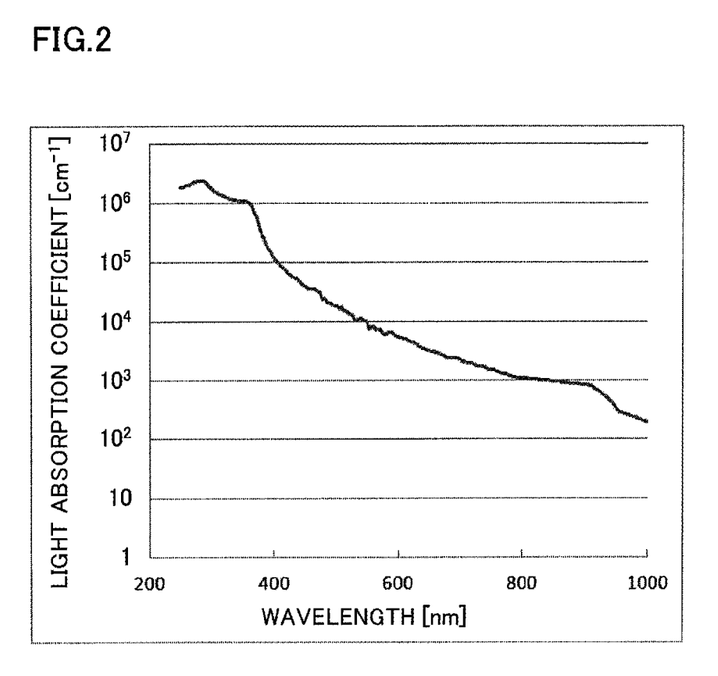
FIG. 2 illustrates a change in the light absorption coefficient of crystalline silicon with respect to the wavelength.

Note that G(x) is the minority carrier generation rate per unit area at the depth x. The minority carrier generation rate G(x) depends on the light absorption coefficient cc of the semiconductor substrate, and the light absorption coefficient cc depends on the wavelength of light. FIG. 2 illustrates a change in the light absorption coefficient of crystalline silicon (i.e., semiconductor substrate) with respect to the wavelength of light. As illustrated in FIG. 2, crystalline silicon has a very large absorption coefficient for ultraviolet rays. Therefore, ultraviolet rays are absorbed by the top surface region of crystalline silicon. On the other hand, crystalline silicon has a small absorption coefficient for infrared rays around the bandgap. Therefore, infrared rays reach a deep region of crystalline silicon.

The light intensity J(x) per unit volume at the depth x when light having an intensity $I_0$ per unit area is applied to the surface of the semiconductor substrate is given by the following expression using the light absorption coefficient α.

$$J(x)=J_0\exp(-\alpha x) \quad (2)$$

Note that $J_0$ ($=I_0/\alpha$) is the volume intensity of light at the surface of the semiconductor substrate. The minority carrier generation rate G(x) is proportional to the light intensity J(x). Specifically, the minority carrier generation rate G(x) increases (a larger number of carriers are generated) as the light intensity J(x) increases. The minority carrier generation rate G(x) is given by the following expression using the light intensity J(x), the photon energy hv (where, h is the Planck's constant, and v is the optical frequency) corresponding to the wavelength, and the carrier generation internal quantum efficiency η.

$$G(x)=J(x)\times h^{-1}\times v^{-1}\times \eta \quad (3)$$

The surface recombination velocities $S_{top}$ and $S_{rear}$ that depend on surface defects of the semiconductor substrate are given as differential coefficient boundary conditions at the surface of the semiconductor substrate (see the following expressions).

$$D\frac{\partial n(x)}{\partial x}\bigg|_{x=0} = S_{top}n(0) \quad (4)$$

$$D\frac{\partial n(x)}{\partial x}\bigg|_{x=d} = -S_{rear}n(d) \quad (5)$$

Note that d is the thickness of the semiconductor substrate.

Specifically, the carrier volume concentration n(x) can be calculated by solving the expression (1) using the minority carrier generation rate G(x) corresponding to the wavelength utilizing the expressions (4) and (5) as the boundary conditions.

The sheet carrier density N (unit: $cm^{-2}$) obtained by integrating the carrier volume concentration n(x) in the depth direction of the semiconductor substrate, and the carrier generation rate H per unit area (unit: $cm^{-2}s^{-1}$) obtained by integrating the minority carrier generation rate G(x) in the depth direction of the semiconductor substrate are given by the following expressions.

$$N=\int_0^d n(x)dx \quad (6)$$

$$H=\int_0^d G(x)dx \quad (7)$$

The effective carrier lifetime $\tau_{eff}$ is calculated using the following expression.

$$N=H\times\tau_{eff} \quad (8)$$

For example, the expressions (1) to (5) are programmed using a finite element difference method, the carrier volume concentration n(x) is calculated using the bulk carrier lifetime $\tau_b$ and the surface recombination velocities $S_{top}$ and $S_{rear}$ as parameters, and the sheet carrier density N is calculated by integrating the carrier volume concentration n(x). The carrier generation rate H is calculated by integrating the minority carrier generation rate G(x), and the sheet carrier density N and the carrier generation rate H are substituted into the expression (8) to calculate the effective carrier lifetime $\tau_{eff}$ (calculated value). When light within a wavelength band for which the semiconductor substrate has a large absorption coefficient is applied to the semiconductor substrate, the effective carrier lifetime $\tau_{eff}$ is given by the following expression.

$$\tau_{eff} = \tau_b \frac{\sqrt{\frac{D}{\tau_b}}\left(1-\exp\left(-\frac{d}{\sqrt{D\tau_b}}\right)\right)}{\left(\sqrt{\frac{D}{\tau_b}}+S_{rear}+\left(\sqrt{\frac{D}{\tau_b}}-S_{rear}\right)\exp\left(-\frac{d}{\sqrt{D\tau_b}}\right)\right)} \quad (9)$$

$$\left(\sqrt{\frac{D}{\tau_b}}+S_{rear}\right)\left(\sqrt{\frac{D}{\tau_b}}+S_{top}\right)-$$

$$\left(\sqrt{\frac{D}{\tau_b}}-S_{top}\right)\left(\sqrt{\frac{D}{\tau_b}}-S_{rear}\right)\exp\left(-\frac{2d}{\sqrt{D\tau_b}}\right)$$

The calculated value (theoretical value) of the effective carrier lifetime $\tau_{eff}$ calculated using the bulk carrier lifetime $\tau_b$ and the surface recombination velocities $S_{top}$ and $S_{rear}$ as parameters is compared with the measured value of the effective carrier lifetime $\tau_{eff}$ measured from the detected microwave intensity to determine the most probable bulk carrier lifetime $\tau_b$ and surface recombination velocities $S_{top}$ and $S_{rear}$. In the embodiments of the invention, a plurality of types of light that differ in wavelength are applied to the semiconductor substrate, and the minority carrier generation rate G(x) differs depending on the wavelength of light (induction light) applied to the semiconductor substrate. Therefore, the calculated value of the effective carrier lifetime $\tau_{eff}$ differs depending on the wavelength of the induction light. Therefore, the calculated value of the effective carrier lifetime $\tau_{eff}$ calculated corresponding to the wavelength of each light applied to the semiconductor substrate is compared with the measured value of the effective carrier lifetime $\tau_{eff}$ measured corresponding to the wavelength of each light applied to the semiconductor substrate while changing the bulk carrier lifetime $\tau_b$ and the surface recombination velocities $S_{top}$ and $S_{rear}$ (parameters) to determine the bulk carrier lifetime $\tau_b$ and the surface recombination velocities $S_{top}$ and $S_{rear}$ when the calculated value of the effective carrier lifetime $\tau_{eff}$ is in best conformity with the measured value of the effective carrier lifetime $\tau_{eff}$.

For example, when using the configuration illustrated in FIG. 1, the calculated value of the effective carrier lifetime $\tau_{eff}$ calculated based on the wavelength of light emitted from the light source 20 is compared with the measured value of the effective carrier lifetime $\tau_{eff}$ measured when light emitted from the light source 20 is applied to the semiconductor substrate while changing the values of the parameters, and the calculated value of the effective carrier lifetime $\tau_{eff}$ calculated based on the wavelength of light emitted from the light source 22 is compared with the measured value of the effective carrier lifetime $\tau_{eff}$ measured when light emitted from the light source 22 is applied to the semiconductor substrate while changing the values of the parameters to determine the most probable bulk carrier lifetime $\tau_b$ and surface recombination velocities $S_{top}$ and $S_{rear}$.

When the bulk carrier lifetime $\tau_b$ in the expression (1) is the bulk carrier lifetime $\tau_b(x)$ at the depth x from the surface, the depthwise distribution of the bulk carrier time (i.e., the bulk carrier lifetime $\tau_b$ corresponding to each depth x) can be calculated by numerical analysis developed from the above finite element method. In this case, the thickness d of the semiconductor substrate is divided into M (M is a positive integer) layers, and the differential expression (1) is changed to a difference expression corresponding to the thickness d/M of each layer. The above boundary conditions (see the expressions (4) and (5)) are provided corresponding to the front side and the back side. Specifically, the carrier volume concentration n(d) that satisfies the boundary condition represented by the expression (5) is presumed, and the carrier volume concentration nM (i.e., the carrier volume concentration in the Mth layer), the carrier volume concentration nM−1 (i.e., the carrier volume concentration in the (M−1)th layer), . . . , and n1 (i.e., the carrier volume concentration in the first layer) are sequentially calculated while changing the initial value little by little to satisfy the difference expression (1). A value that satisfies the boundary condition represented by the expression (4) is determined to be the numerical solution.

A specific method that measures the effective carrier lifetime $\tau_{eff}$ is described below. The measured value of the effective carrier lifetime $\tau_{eff}$ can be accurately calculated when the sheet carrier density N and the carrier generation rate H are known (see the expression (8)). However, the carrier generation rate H depends on the photon flux F of incident light, the carrier generation internal quantum efficiency η, and the light reflection loss R (see the following expression).

$$H = F \times \eta \times (1-R) \quad (10)$$

Since the carrier generation internal quantum efficiency η depends on the semiconductor substrate, and the light reflection loss R depends on the refractive index, the light absorption coefficient, the thickness, and the surface shape, it is not easy to accurately measure the carrier generation rate H. The carrier generation rate H can be accurately measured by applying the effective carrier lifetime ($\tau_{eff}$) measurement method disclosed in J. M. Borrego, R. J. Gutmann, N. Jensen, and O. Paz: *Solid-Sate Electron.*, 30, 195 (1987) that utilizes a periodic pulse method. According to the periodic pulse method, it is possible to measure the effective carrier lifetime $\tau_{eff}$ through weak irradiation at the same level as that of continuous light irradiation. However, the periodic pulse method is not suitable for the measurement of a very short effective carrier lifetime $\tau_{eff}$ of less than 10 microseconds. In order to deal with this problem, the inventor developed an effective carrier lifetime ($\tau_{eff}$) measurement method that utilizes a reference sample similar to the measurement target sample.

According to this method, when the measurement target sample is crystalline silicon, single-crystal silicon is used as the reference sample. A passivation film (e.g., thermal oxide film) is formed on the surface of the reference sample so that carrier recombination surface defects can be suppressed, and a long effective carrier lifetime $\tau_{eff}$ can be obtained. When an oxide film is formed on the measurement target sample, the thermal oxide film is formed on the reference sample to have the same thickness as that of the oxide film formed on the measurement target sample. When the measurement target sample is a bare semiconductor, a thin oxide film that does not affect the reflectance (e.g., a thermal oxide film having a thickness of 10 nm) is formed on the reference sample. When the surface of the measurement target sample has irregularities (e.g., texture), a similar texture is formed on the reference sample.

The effective carrier lifetime $\tau_{eff}$ of the reference sample is measured using the periodic pulse method. Since effective carrier lifetime $\tau_{eff}$ normally changes depending on the light intensity, the average light intensity when implementing the periodic pulse method is set to be the same as the light intensity of continuous light described later. Continuous light is applied to the reference sample, and microwave absorption measurement is performed to calculate the sheet carrier density N of the reference sample. The sheet carrier density N and the measured value of the effective carrier lifetime $\tau_{eff}$ are substituted into the expression (8) to calculate the carrier generation rate H when continuous light is applied.

Continuous light is applied to the measurement target sample, and microwave absorption measurement is performed to calculate the sheet carrier density N of the measurement target sample. The sheet carrier density N and the carrier generation rate H of the measurement target sample are substituted into the expression (8) to calculate the effective carrier lifetime $\tau_{eff}$ of the measurement target sample. According to this method, the effective carrier lifetime $\tau_{eff}$ of the measurement target sample can be accurately measured using an accurate carrier generation rate H.

3. Measurement Results 3-1. Example 1

A semiconductor substrate of which the surface was passivated was used as a first sample. The first sample was subjected to a heat treatment to prepare a second sample. The effective carrier lifetime, the bulk carrier lifetime, and the surface recombination velocity of each sample were measured using the measurement device according to one embodiment of the invention.

Figure 3:
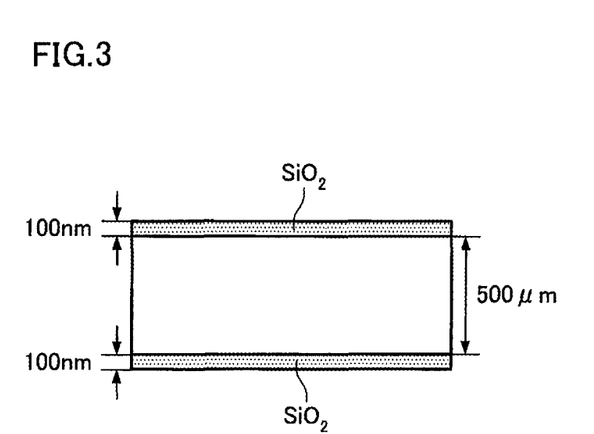
FIG. 3 is a diagram illustrating a semiconductor substrate that was subjected to measurement using a measurement device according to one embodiment of the invention.

An n-type silicon substrate (thickness: 500 micrometers) of which each side was coated with a thermal oxide film (thickness: 100 nm) (see FIG. 3) was used as the first sample. The second sample was prepared by applying laser light having a wavelength of 940 nm to the entire surface of the first sample (see FIG. 3) at a high intensity of $5 \times 10^4$ W/cm$^2$ (heat treatment). It has been known from related-art literature that the effective carrier lifetime decreases due to a heat treatment utilizing laser irradiation.

An oscillator that generates 9.35 GHz microwaves was used as the microwave generation section 10. A laser light source that emits laser light having a wavelength of 635 nm was used as the light source 20 that emits light having a short wavelength, and a laser light source that emits laser light having a wavelength of 980 nm was used as the light source 22 that emits light having a long wavelength. Light having a wavelength of 635 nm has a small penetration depth into silicon of 2.7 micrometers, and is absorbed by the top surface region of the silicon substrate, and light having a wavelength of 980 nm has a large penetration depth into silicon of 90 micrometers, and reaches a deep region of the silicon substrate.

Figure 4:
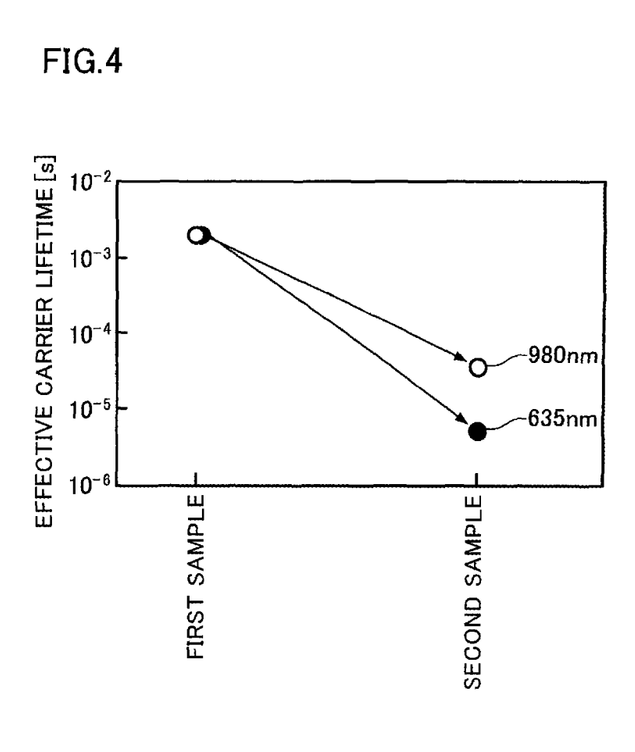
FIG. 4 illustrates the effective carrier lifetime measurement results obtained using a measurement device according to one embodiment of the invention.

FIG. 4 illustrates the measurement results for the effective carrier lifetime when light having a wavelength of 635 nm was applied to the first sample and the second sample, and the effective carrier lifetime when light having a wavelength of 980 nm was applied to the first sample and the second sample. In FIG. 4, each white circle indicates the measurement result when light having a wavelength of 980 nm was applied, and each black circle indicates the measurement result when light having a wavelength of 635 nm was applied.

As illustrated in FIG. 4, the n-type silicon substrate (first sample) that was coated with the thermal oxide film had a long effective carrier lifetime of 2 ms, and the effective carrier lifetime when light having a wavelength of 635 nm was applied and the effective carrier lifetime when light having a wavelength of 980 nm was applied were almost identical. On the other hand, the n-type silicon substrate (second sample) that was subjected to the heat treatment utilizing laser irradiation had an effective carrier lifetime of 5 microseconds when light having a wavelength of 635 nm was applied, and had an effective carrier lifetime of 35 microseconds when light having a wavelength of 980 nm was applied. It was thus confirmed that the effective carrier lifetime decreased due to the heat treatment utilizing laser irradiation, and the effective carrier lifetime when light having a long wavelength was applied was longer than that when light having a short wavelength was applied.

The effective carrier lifetimes measured using the first sample were compared with the effective carrier lifetime calculated for light having a wavelength of 635 nm and the effective carrier lifetime calculated for light having a wavelength of 980 nm to determine the bulk carrier lifetime $\tau_b$ and the surface recombination velocities $S_{top}$ and $S_{rear}$ that were in best conformity with the measured effective carrier lifetimes using the above analytical method. It was found that the bulk carrier lifetime $\tau_b$ was 20 ms, and the surface recombination velocities $S_{top}$ and $S_{rear}$ were respectively 12.3 cm/s.

Likewise, the bulk carrier lifetime $\tau_b$ and the surface recombination velocities $S_{top}$ and $S_{rear}$ that were in best conformity with the effective carrier lifetimes measured using the second sample were determined using the above analytical method. It was found that the surface recombination velocity $S_{top}$ of the irradiation side of the second sample was 25,000 cm/s. It was thus confirmed that the surface recombination velocity of the irradiation side increased due to the heat treatment utilizing laser irradiation.

Figure 5A:
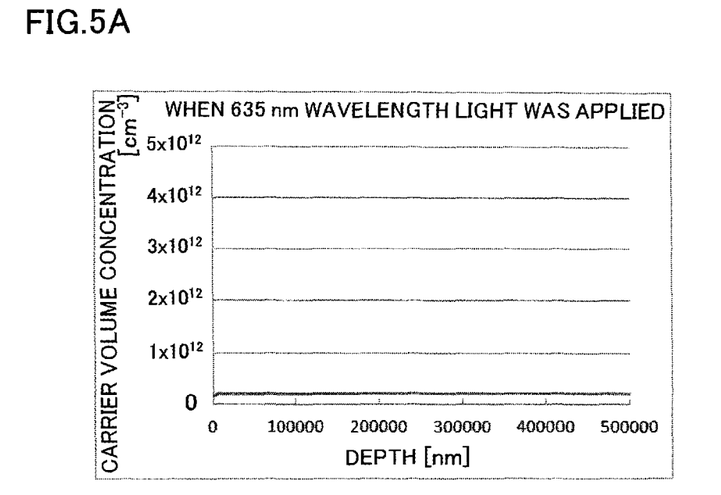
FIG. 5A illustrates the carrier volume concentration measurement results obtained using a measurement device according to one embodiment of the invention.
Figure 5B:
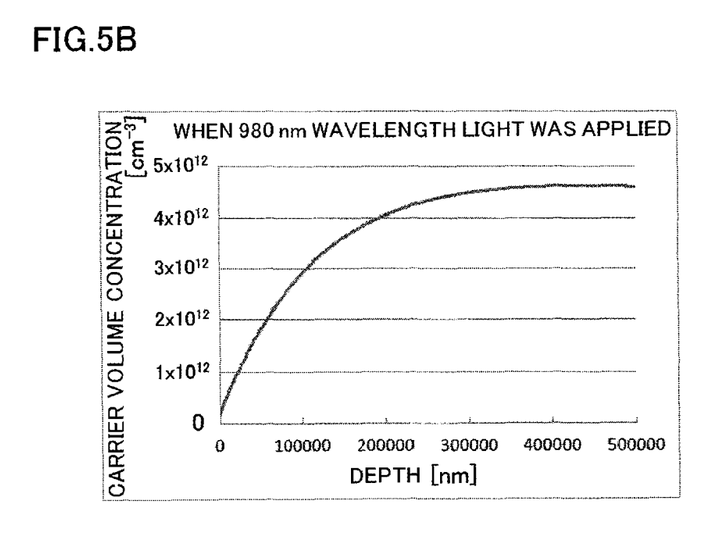
FIG. 5B illustrates the carrier volume concentration measurement results obtained using a measurement device according to one embodiment of the invention.

FIGS. 5A and 5B illustrate the distribution of the carrier volume concentration n(x) with respect to the depth x determined from the analysis results obtained using the second sample. FIG. 5A illustrates the distribution of the carrier volume concentration n(x) when light having a wavelength of 635 nm was applied, and FIG. 5B illustrates the distribution of the carrier volume concentration n(x) when light having a wavelength of 980 nm was applied.

As illustrated in FIG. 5A, since the light absorption coefficient of the silicon substrate was large when light having a wavelength of 635 nm was applied, and carriers were generated in the surface region of the substrate, the carrier volume concentration decreased due to the high surface recombination velocity $S_{top}$. As illustrated in FIG. 5B, since the light absorption coefficient of the silicon substrate was small when light having a wavelength of 980 nm was applied, light reached a deep region of the silicon substrate, and carriers were generated in the silicon bulk. Therefore, the carriers survived through diffusion until the carriers reached the surface of the silicon substrate, and the carrier volume concentration and the effective carrier lifetime increased.

It was thus confirmed that both the bulk carrier lifetime and the surface recombination velocity of the semiconductor substrate can be measured using the measurement device and the measurement method according to the embodiments of the invention without presuming the bulk carrier lifetime or the surface recombination velocity.

3-2. Example 2

In Example 2, a silicon substrate (thickness: 700 micrometers) that was coated with a thermal oxide film was used as a sample. Silicon atoms (ions) were implanted into the silicon substrate at a dose of 70 keV (implantation amount: $1 \times 10^{14}$ cm$^{-2}$). The effective carrier lifetime $\tau_{eff}$ of the sample was measured before and after ion implantation while applying light having a wavelength of 635 nm or light having a wavelength of 980 nm. The measurement results were analyzed using the finite element method to determine the surface recombination velocities $S_{top}$ and $S_{rear}$ and the depthwise distribution $\tau_b(x)$ of the bulk carrier lifetime. The thickness of the substrate was divided into a plurality of layers, and the distribution $\tau_b(x)$ of the bulk carrier lifetime was calculated corresponding to each layer. The measurement results and the analysis results are shown in Table 1.

TABLE 1

| | Measured value | | Analytical value | | | |
|---|---|---|---|---|---|---|
| Sample | $\tau_{\mathit{eff}}$ (635 nm) | $\tau_{\mathit{eff}}$ (980 nm) | $S_{top}$ (cm/s) | $S_{rear}$ (cm/s) | $\tau_b$ (first layer) | $\tau_b$ (second layer) |
| Before ion implantation | 1.6E−04 | 1.7E−04 | 190 | 190 | 1.0E−03 | |
| After ion implantation | 9.0E−07 | 6.0E−06 | 10000 | 190 | 1.0E−05 | 1.0E−03 |

In Table 1, the first layer refers to a layer having a depth x (from the surface) of 0 to 490 micrometers, and the second layer refers to a layer having a depth x (from the surface) of 490 to 700 micrometers.

A long effective carrier lifetime $\tau_{\mathit{eff}}$ was obtained before ion implantation when applying light having a wavelength of 635 nm, and when applying light having a wavelength of 980 nm. The measured values were analyzed, and it was found that the surface recombination velocities $S_{top}$ and $S_{rear}$ were 190 cm/s. The surface recombination velocities $S_{top}$ and $S_{rear}$ were in good conformity with the measured values when the bulk carrier lifetime $\tau_b$ was 1 ms over the entire substrate in the thickness direction.

The effective carrier lifetime $\tau_{\mathit{eff}}$ significantly decreased after ion implantation. In particular, the effective carrier lifetime $\tau_{\mathit{eff}}$ was short when applying light having a wavelength of 980 nm. This suggests that the bulk carrier lifetime $\tau_b$ decreased from the surface region to a deep region of the silicon substrate. The measured values were analyzed, and it was found that the bulk carrier lifetime $\tau_b$ decreased to 10 microseconds up to a depth of 490 micrometers from the surface. Since silicon atoms (ions) are implanted only up to a depth of about 0.1 micrometers, it was confirmed by the above measurement that carrier recombination defects were formed due to high-energy ion up to a region significantly deeper than the implantation depth.

3-3. Example 3

In Example 3, an n-type silicon substrate (thickness: 500 micrometers) that was coated with a thermal oxide film (thickness: 100 nm) was used as a sample. Argon plasma was applied to the silicon substrate for 1 minute at an output of 50 W. The effective carrier lifetime $\tau_{\mathit{eff}}$ of the sample was measured before and after the plasma treatment while applying light having a wavelength of 635 nm or light having a wavelength of 980 nm. The measurement results were analyzed using the finite element method to determine the surface recombination velocities $S_{top}$ and $S_{rear}$ and the bulk carrier lifetime $\tau_b$. The measurement results and the analysis results are shown in Table 2.

TABLE 2

| | Measured value | | Analytical value | | |
|---|---|---|---|---|---|
| Sample | $\tau_{\mathit{eff}}$ (635 nm) | $\tau_{\mathit{eff}}$ (980 nm) | $S_{top}$ (cm/s) | $S_{rear}$ (cm/s) | $\tau_b$ |
| Before plasma treatment | 3.10E−03 | 3.10E−03 | 8 | 8 | 0.1 |
| After plasma treatment | 6.00E−06 | 4.20E−05 | 8000 | 8 | 0.1 |

A long effective carrier lifetime $\tau_{\mathit{eff}}$ was obtained before the plasma treatment when applying light having a wavelength of 635 nm, and when applying light having a wavelength of 980 nm. The measured values were analyzed, and it was found that the surface recombination velocities $S_{top}$ and $S_{rear}$ were 8 cm/s. The surface recombination velocities $S_{top}$ and $S_{rear}$ were in good conformity with the measured values when the bulk carrier lifetime $\tau_b$ was 100 ms over the entire substrate in the thickness direction.

The effective carrier lifetime $\tau_{\mathit{eff}}$ significantly decreased after the plasma treatment. In particular, the effective carrier lifetime $\tau_{\mathit{eff}}$ was short when applying light having a wavelength of 635 nm. This suggests that defects were localized in the surface region of the silicon substrate. The measured values were analyzed, and it was found that the bulk carrier lifetime $\tau_b$ and the surface recombination velocity $S_{rear}$ did not change due to the plasma treatment, and only the surface recombination velocity $S_{top}$ increased to 8000 cm/s. It was confirmed by the above measurement that carrier recombination defects were formed in the surface region of the silicon substrate due to the argon plasma treatment.

4. Modifications

The invention is not limited to the above embodiments, and various modifications and variations may be made of the above embodiments. The invention includes configurations that are substantially identical (e.g., in function, method and effect, or objective and effect) with the configurations described in connection with the above embodiments. The invention also includes a configuration in which an unsubstantial element of the above embodiments is replaced by another element. The invention also includes a configuration having the same effects as those of the configurations described in connection with the above embodiments, or a configuration capable of achieving the same object as those of the configurations described in connection with the above embodiments. The invention further includes a configuration obtained by adding known technology to the configurations described in connection with the above embodiments.

For example, the measurement device 1 illustrated in FIG. 1 may include an X-axis moving stage that moves the semiconductor substrate S in the X-axis direction in FIG. 1, and a Y-axis moving stage that moves the semiconductor substrate S in the Y-axis direction in FIG. 1. According to this configuration, measurement can be performed on an arbitrary position of the semiconductor substrate S in the XY plane. The measurement device 1 may be configured to subject light emitted from the light source 20 and light emitted from the light source 22 to pulse modulation, and implement lock-in detection of the microwave intensity. The measurement device 1 may include two or more light sources that respectively apply light that has a different wavelength and generates photoinduced carriers.

The invention claimed is:

1. A photoinduced carrier lifetime measurement device that measures an effective carrier lifetime of photoinduced carriers generated in a semiconductor substrate, the photoinduced carrier lifetime measurement device comprising:
    first and second light sources configured to respectively apply at least two types of continuous light to the semiconductor substrate, the at least two types of continuous light differing in wavelength, and generating the photoinduced carriers;

an oscillator configured to generate microwaves that are applied to the semiconductor substrate;

a detection section that detects an intensity of the microwaves that have passed through the semiconductor substrate; and a computing device configured to calculate the effective carrier lifetime based on the intensity of the microwaves detected by the detection section, the computing device further configured to calculate the effective carrier lifetime corresponding to the wavelength of each of the at least two types of continuous light based on a change in the intensity of the microwaves detected when applying each of the at least two types of continuous light applied to the semiconductor substrate from respective ones of the first light source and the second light source, and to calculate a bulk carrier lifetime and a surface recombination velocity of the semiconductor substrate based on the effective carrier lifetime calculated corresponding to the wavelength of each of the at least two types of continuous light applied to the semiconductor substrate from the respective ones of the first light source and the second light source, wherein the computing device is further configured to compare a calculated value of the effective carrier lifetime calculated corresponding to the wavelength of each of the at least two types of continuous light applied to the semiconductor substrate from the respective ones of the first light source and the second light source using the bulk carrier lifetime and the surface recombination velocity as parameters with a measured value of the effective carrier lifetime calculated corresponding to the wavelength of each of the at least two types of continuous light applied to the semiconductor substrate from the respective ones of the first light source and the second light source based on the detected intensity of the microwaves while changing values of the parameters to determine the bulk carrier lifetime and the surface recombination velocity when the calculated value of the effective carrier lifetime calculated corresponding to the wavelength of each of the at least two types of continuous light applied to the semiconductor substrate from the respective ones of the first light source and the second light source is closest to the measured value of the effective carrier lifetime calculated corresponding to the wavelength of each of the at least two types of continuous light applied to the semiconductor substrate from the respective ones of the first light source and the second light source.

2. The photoinduced carrier lifetime measurement device as defined in claim 1, wherein the computing device is further configured to calculate a carrier generation rate based on an effective carrier lifetime of a reference sample, prepared by forming a passivation film on a surface of the semiconductor substrate, that is calculated based on the intensity of the microwaves detected when applying periodic pulsed light to the reference sample, and a sheet carrier density of the reference sample calculated based on the intensity of the microwaves detected when applying continuous light to the reference sample, and to calculate the measured value of the effective carrier lifetime based on a sheet carrier density of the semiconductor substrate as a measurement target sample calculated based on the intensity of the microwaves detected when applying continuous light to the semiconductor substrate, and the carrier generation rate.

3. The photoinduced carrier lifetime measurement device as defined in claim 1, wherein the at least two types of continuous light differ in absorption coefficient with respect to the semiconductor substrate.

4. The photoinduced carrier lifetime measurement device as defined in claim 3, wherein the at least two types of continuous light differ in the absorption coefficient with respect to the semiconductor substrate by a factor of at least 2.

5. A photoinduced carrier lifetime measurement device that measures an effective carrier lifetime of photoinduced carriers generated in a semiconductor substrate, the photoinduced carrier lifetime measurement device comprising:

first and second light sources configured to respectively apply at least two types of continuous light to the semiconductor substrate, the at least two types of continuous light differing in wavelength, and generating the photoinduced carriers;

an oscillator configured to generate microwaves that are applied to the semiconductor substrate;

a detection section that detects an intensity of the microwaves that have passed through the semiconductor substrate; and a computing device configured to calculate the effective carrier lifetime based on the intensity of the microwaves detected by the detection section, the computing device further configured to calculate the effective carrier lifetime corresponding to the wavelength of each of the at least two types of continuous light based on a change in the intensity of the microwaves detected when applying each of the at least two types of continuous light applied to the semiconductor substrate from respective ones of the first light source and the second light source, and calculating a bulk carrier lifetime and a surface recombination velocity of the semiconductor substrate based on the effective carrier lifetime calculated corresponding to the wavelength of each of the at least two types of continuous light applied to the semiconductor substrate from the respective ones of the first light source and the second light source, wherein the computing device is further configured to compare a calculated value of the effective carrier lifetime calculated corresponding to the wavelength of each of the at least two types of continuous light applied to the semiconductor substrate from the respective ones of the first light source and the second light source using a depthwise distribution of the bulk carrier lifetime and the surface recombination velocity as parameters with a measured value of the effective carrier lifetime calculated corresponding to the wavelength of each of the at least two types of continuous light applied to the semiconductor substrate from the respective ones of the first light source and the second light source based on the detected intensity of the microwaves while changing values of the parameters to determine the depthwise distribution of the bulk carrier lifetime and the surface recombination velocity when the calculated value of the effective carrier lifetime calculated corresponding to the wavelength of each of the at least two types of continuous light applied to the semiconductor substrate from respective ones of the first light source and the second light source is closest to the measured value of the effective carrier lifetime calculated corresponding to the wavelength of each of the at least two types of continuous light applied to the semiconductor substrate from respective ones of the first light source and the second light source.

6. The photoinduced carrier lifetime measurement device as defined in claim 5,
wherein the computing device is further configured to calculate a carrier generation rate based on an effective carrier lifetime of a reference sample, prepared by forming a passivation film on a surface of the semiconductor substrate, that is calculated based on the intensity of the microwaves detected when applying periodic pulsed light to the reference sample, and a sheet carrier density of the reference sample calculated based on the intensity of the microwaves detected when applying continuous light to the reference sample, and to calculate the measured value of the effective carrier lifetime based on a sheet carrier density of the semiconductor substrate as a measurement target sample calculated based on the intensity of the microwaves detected when applying continuous light to the semiconductor substrate, and the carrier generation rate.

7. A photoinduced carrier lifetime measurement method that measures an effective carrier lifetime of photoinduced carriers generated in a semiconductor substrate, the photoinduced carrier lifetime measurement method comprising:
applying, using first and second light sources of a measurement device, at least two types of continuous light to the semiconductor substrate, and applying microwaves to the semiconductor substrate, the at least two types of continuous light differing in wavelength, and generating the photoinduced carriers;
detecting an intensity of the microwaves that have passed through the semiconductor substrate; and
calculating the effective carrier lifetime corresponding to the wavelength of each of the at least two types of continuous light, as applied to the semiconductor substrate using the first and second light sources of the measurement device, based on a change in the intensity of the microwaves detected when applying each of the at least two types of continuous light to the semiconductor substrate from respective ones of the first light source and the second light source, and calculating a bulk carrier lifetime and a surface recombination velocity of the semiconductor substrate based on the effective carrier lifetime calculated corresponding to the wavelength of each of the at least two types of continuous light applied to the semiconductor substrate from the respective ones of the first light source and the second light source; and
comparing a calculated value of the effective carrier lifetime calculated corresponding to the wavelength of each of the at least two types of continuous light applied to the semiconductor substrate from the respective ones of the first light source and the second light source using the bulk carrier lifetime and the surface recombination velocity as parameters with a measured value of the effective carrier lifetime calculated corresponding to the wavelength of each of the at least two types of continuous light applied to the semiconductor substrate from the respective ones of the first light source and the second light source based on the detected intensity of the microwaves while changing values of the parameters to determine the bulk carrier lifetime and the surface recombination velocity when the calculated value of the effective carrier lifetime calculated corresponding to the wavelength of each of the at least two types of continuous light applied to the semiconductor substrate from the respective ones of the first light source and the second light source is closest to the measured value of the effective carrier lifetime calculated corresponding to the wavelength of each of the at least two types of continuous light applied to the semiconductor substrate from the respective ones of the first light source and the second light source.

8. The photoinduced carrier lifetime measurement method as defined in claim 7, further comprising:
comparing a calculated value of the effective carrier lifetime calculated corresponding to the wavelength of each of the at least two types of continuous light using a depthwise distribution of the bulk carrier lifetime and the surface recombination velocity as parameters with a measured value of the effective carrier lifetime calculated corresponding to the wavelength of each of the at least two types of continuous light based on the detected intensity of the microwaves while changing values of the parameters to determine the depthwise distribution of the bulk carrier lifetime and the surface recombination velocity when the calculated value of the effective carrier lifetime calculated corresponding to the wavelength of each of the at least two types of continuous light is closest to the measured value of the effective carrier lifetime calculated corresponding to the wavelength of each of the at least two types of continuous light.

9. The photoinduced carrier lifetime measurement method as defined in claim 8, further comprising:
calculating a carrier generation rate based on an effective carrier lifetime of a reference sample, prepared by forming a passivation film on a surface of the semiconductor substrate, that is calculated based on the intensity of the microwaves detected when applying periodic pulsed light to the reference sample, and a sheet carrier density of the reference sample calculated based on the intensity of the microwaves detected when applying continuous light to the reference sample, and calculating the measured value of the effective carrier lifetime based on a sheet carrier density of the semiconductor substrate as a measurement target sample calculated based on the intensity of the microwaves detected when applying continuous light to the semiconductor substrate, and the carrier generation rate.

10. The photoinduced carrier lifetime measurement method as defined in claim 7, further comprising:
calculating a carrier generation rate based on an effective carrier lifetime of a reference sample, prepared by forming a passivation film on a surface of the semiconductor substrate, that is calculated based on the intensity of the microwaves detected when applying periodic pulsed light to the reference sample, and a sheet carrier density of the reference sample calculated based on the intensity of the microwaves detected when applying continuous light to the reference sample, and calculating the measured value of the effective carrier lifetime based on a sheet carrier density of the semiconductor substrate as a measurement target sample calculated based on the intensity of the microwaves detected when applying continuous light to the semiconductor substrate, and the carrier generation rate.

11. The photoinduced carrier lifetime measurement method as defined in claim 7, wherein the at least two types of continuous light differ in absorption coefficient with respect to the semiconductor substrate.

12. The photoinduced carrier lifetime measurement method as defined in claim 11, wherein the at least two types of continuous light differ in the absorption coefficient with respect to the semiconductor substrate by a factor of at least 2.

* * * * *